(12) United States Patent
Wendell et al.

(10) Patent No.: US 9,421,367 B1
(45) Date of Patent: Aug. 23, 2016

(54) METHOD AND APPARATUS FOR PERFORMING MICROCURRENT ELECTROTHERAPY

(75) Inventors: Keith F. Wendell, Pacific Palisades, CA (US); David G. Estes, Oroville, CA (US)

(73) Assignee: ELECTROREGENESIS, INC., Pacific Palisades, CA (US)

(*) Notice: Subject to any disclaimer, the term of this patent is extended or adjusted under 35 U.S.C. 154(b) by 0 days.

(21) Appl. No.: 09/656,519

(22) Filed: Sep. 7, 2000

Related U.S. Application Data

(63) Continuation-in-part of application No. 09/645,819, filed on Aug. 24, 2000, now abandoned.

(51) Int. Cl.
*A61N 1/22* (2006.01)
*A61N 1/36* (2006.01)
(Continued)

(52) U.S. Cl.
CPC ............ *A61N 1/36014* (2013.01); *A61N 1/321* (2013.01); *A61N 1/326* (2013.01); *A61N 1/0468* (2013.01)

(58) Field of Classification Search
CPC ... A61N 1/326; A61N 1/321; A61N 1/36014; A61N 1/0468
USPC .......... 600/382, 384, 386, 390; 607/2, 43, 45, 607/46, 48, 50, 149, 152, 72, 74, 76, 118; 606/32, 34
See application file for complete search history.

(56) References Cited

U.S. PATENT DOCUMENTS

| 3,958,577 A | 5/1976 | Rodler .......................... 128/420 |
| 4,014,323 A | 3/1977 | Gilmer et al. .............. 128/2.1 Z |
| 4,240,437 A | 12/1980 | Church .......................... 128/420 |

(Continued)

FOREIGN PATENT DOCUMENTS

| WO | WO 84/01298 | 12/1984 |
| WO | PCT/US01/42099 | 8/2002 |

OTHER PUBLICATIONS

Robert O. Becker, M.d., and Gary Selden, "The Body Electric", 1985, pp. 118-149 and pp. 203-214.
(Continued)

*Primary Examiner* — Edward Moran
*Assistant Examiner* — Michael Carey
(74) *Attorney, Agent, or Firm* — Steven M. Greenberg, Esq.; CRGO Law

(57) ABSTRACT

An electrotherapy method and apparatus for healing injuries and tissue diseases to the human or animal body is disclosed. Particularly, the electrotherapy method disclosed herein comprises delivering a current under various conditions, such as, applying microcurrents ranging from 4 milliamperes to 1 femtoamperes, applying an alternating current with a frequency in the range of 0.00065 Hz to 0.00085 Hz, utilizing large surface-area electrodes to achieve low current densities of less than 5 microamperes per square inch. The apparatus of the present invention includes a plurality of electrode wraps for applying said electrotherapy method to a body. Each electrode wrap includes a first layer wrap of water absorptive material and a second layer wrap of moderately conductive material. Each electrode wrap is placed on a portion of the body, including, without limitation, arms, legs, hands, feet and torso. The method and apparatus of the present invention are useful in treating wounds, ulcerations, spinal cord injuries, amyotrophic lateral sclerosis, multiple sclerosis, nervous system abnormalities, scar tissue and age lines.

4 Claims, 3 Drawing Sheets

(51) Int. Cl.
*A61N 1/32* (2006.01)
*A61N 1/04* (2006.01)

(56) References Cited

U.S. PATENT DOCUMENTS

| | | | | |
|---|---|---|---|---|
| 4,308,868 A | * | 1/1982 | Jhabvala | 128/421 |
| 4,422,461 A | * | 12/1983 | Glumac | 128/798 |
| 4,556,064 A | | 12/1985 | Pomeranz et al. | 128/423 |
| 4,676,246 A | | 6/1987 | Korenaga | 128/399 |
| 4,817,594 A | * | 4/1989 | Juhasz | 128/155 |
| 4,846,181 A | | 7/1989 | Miller | 128/421 |
| 4,907,601 A | | 3/1990 | Frick | 128/783 |
| 4,960,124 A | | 10/1990 | Masaki | 128/421 |
| 4,960,125 A | | 10/1990 | Masaki | 128/421 |
| 4,982,742 A | | 1/1991 | Claude | 128/798 |
| 5,010,896 A | * | 4/1991 | Westbrook | 128/798 |
| 5,014,699 A | | 5/1991 | Pollack et al. | 128/419 |
| 5,038,797 A | * | 8/1991 | Batters | 128/798 |
| 5,133,351 A | | 7/1992 | Masaki | 128/419 |
| 5,186,171 A | | 2/1993 | Kuhry | 128/421 |
| 5,354,321 A | | 10/1994 | Berger | 607/75 |
| 5,362,420 A | | 11/1994 | Itoh et al. | 252/500 |
| 5,387,231 A | | 2/1995 | Sporer | 607/48 |
| 5,395,398 A | * | 3/1995 | Rogozinski | 607/50 |
| 5,397,338 A | | 3/1995 | Grey et al. | 607/115 |
| 5,476,481 A | | 12/1995 | Schondorf | 607/2 |
| 5,573,552 A | | 11/1996 | Hansjurgens | 607/68 |
| 5,674,261 A | | 10/1997 | Smith | 607/46 |
| 5,728,141 A | | 3/1998 | Calbet Benach et al. | 607/98 |
| 5,741,317 A | | 4/1998 | Ostrow | 607/85 |
| 5,891,182 A | * | 4/1999 | Fleming | A61N 1/326 128/903 |
| 5,906,638 A | | 5/1999 | Shimoda | 607/152 |
| 5,935,156 A | * | 8/1999 | Chandler et al. | 607/66 |
| 6,004,257 A | * | 12/1999 | Jacobson | 600/9 |
| 6,142,927 A | * | 11/2000 | Clark | 600/9 |

OTHER PUBLICATIONS

A. R. Hendrickson, Communication from the Australian Patent Office, Nov. 20, 2001, 2 pages.

* cited by examiner

METHOD AND APPARATUS FOR PERFORMING MICROCURRENT ELECTROTHERAPY

The present application is a Continuation-in-Part of U.S. patent application Ser. No. 09/645,819, filed on Aug. 24, 2000, now abandoned, which is incorporated herein in its entirety by reference.

FIELD OF THE INVENTION

The present invention relates to a microcurrent electrotherapy method and apparatus for using extremely low level current and current densities to promote the healing process in a subject in need thereof.

DESCRIPTION OF THE PRIOR ART

Electrotherapy is well known to those skilled in the art as a way of assisting the human body's natural healing process. Prior inventions in the field of electrotherapy have been directed at treating such ailments as pains, lacerations, abrasions, sprains, strains, neurolgia, Parkinson's disease, fatigue, hemorrhoids and the like. Several different methods have been developed for applying electrotherapy to the human body. Some techniques, such as that described in U.S. Pat. No. 5,935,156, which is incorporated herein by reference, teach applying a direct current to the body. Other techniques, such as that described in U.S. Pat. No. 4,960,125, which is incorporated herein by reference, teach applying an alternating current to the body.

The recognized method by which electrotherapy performs its healing functions is by acting on the ions contained within human tissue. Human tissue for the most part is not electrically neutral, but contains charges in the form of positive and negative ions. These positive and negative ions are the life energy force of the body. When an electric current is applied to a body, that current creates a force on the ions in the tissue of that body, causing the ions to be displaced from their original position. The movement of these ions causes, among other things, a warming and stimulation of the tissue, and also assists in the movement of fluids through the body.

However, several problems have been identified with the previously utilized techniques of electrotherapy. It has been recognized that the utilization of direct current through the body can cause the tissue of the body to which the current is applied to break down. Such a result is counter-productive to the goal of increased regeneration and healing of the human body. As an alternative, the application of alternating current to the body is currently the most commonly used method of electrotherapy treatment. However, the application of high-frequency alternating current has been recognized to have minimal therapeutic effect. This is due to the fact that a high frequency alternating current causes the ions of the tissue to oscillate rapidly without being displaced very far from their original positions. Therefore, electrotherapy techniques have been developed that utilize low frequency alternating current. Such a technique is disclosed in U.S. Pat. No. 5,476,481, which is incorporated herein by reference. The known techniques of low-frequency alternating current electrotherapy utilize a low-end frequency of around 0.01 Hz.

The concept of microcurrent electrotherapy is well-known in the art. Microcurrent electrotherapy, also called MENS (microcurrent electrical neuromuscular stimulation), is the use of low-level current to promote healing and regeneration of the human body. The current used in microcurrent electrotherapy is normally in the range of 20 microamperes to 600 microamperes. One benefit of microcurrent electrotherapy over high current electrotherapy techniques is that it results in little or no discomfort to the patient.

Another problem with current electrotherapy techniques is that the current density (current per unit surface area) of these techniques is fairly high. Most electrotherapy techniques, including microcurrent electrotherapy techniques, utilize small electrodes of several square inches of surface area. This translates into a current density of 0.1 milliamperes per square inch to 5 milliamperes per square inch for high current electrotherapy techniques at the point of current application to the body and as the current travels through the body. Current density yields for microcurrent electrotherapy techniques range from 5 microamperes per square inch to 120 microamperes per square inch. The high current densities achieved by the known techniques overload the body's natural electropotential during application. Applicants have discovered that the resulting overload of the body's natural electropotential is counter-productive to stimulation of the body's natural process of tissue healing and regeneration.

SUMMARY OF THE INVENTION

The present invention is a method and apparatus for electrotherapy. The object of the present invention is to improve upon the known techniques of electrotherapy, as well as overcome some of their limitations. To achieve the foregoing in accordance with the present invention, a method and apparatus is provided for healing injuries to the human body, as well as other types of tissue. It is understood that the method and apparatus of the present invention can also be used for veterinary purposes. A method and apparatus is also provided for stimulating regeneration and growth of otherwise unhealthy tissue. Particularly, the method and apparatus of the present invention is useful in treating wounds, ulcerations, spinal cord injuries, amyotrophic lateral sclerosis, multiple sclerosis, nervous system abnormalities, scar tissue and age lines.

In one aspect of the present invention, a method is disclosed which includes delivering a microcurrent under specific conditions, such as: applying microcurrents ranging from 3 milliamperes to 1 femtoamperes, applying an alternating current with a frequency in the range of 0.00065 Hz to 0.00085 Hz and utilizing large surface-area electrodes, referred to herein as electrode wraps, to achieve low current densities. The use of currents lower than 20 microamperes is currently unknown in the prior art. Prior techniques have also not utilized the very low current frequency and current densities of the present invention for any current level.

In another aspect of the present invention, an apparatus is disclosed which includes a plurality of electrode wraps for applying said electrotherapy method to a body. Each electrode wrap includes a first layer wrap of water absorptive material and a second layer wrap of moderately conductive material. Each electrode wrap is placed on a portion of the body, including, without limitation, arms, legs, hands, feet and torso. The first and second layers of the electrode wrap are applied to the selected portion of the body in such a way that each forms a closed surface around the body part to which they are applied. An electropotential is then applied across the electrode wraps to generate a current flow through the body. The area of application of the electrode wraps to the selected portion of the body is large compared to the area covered by known electrotherapy electrodes.

In yet another aspect of the present invention, a means for generating electric current for a microcurrent therapy is disclosed. The current output generator ("COG") is the preferred device for generating a constant current and outputting said current to the electrode wraps according to the method of the present invention. The current is provided to the electrode wraps from the COG by means for conducting current, such as a rubber-encased copper wire, which is electrically connected to either the positive or negative lead from the current output generator. Particularly, the COG is designed to deliver current according to the method of the present invention.

The method of the present invention teaches a constant current in the range of 3 milliamperes to 1 femtoampere. When these low current levels are utilized with the large surface area of the electrode wraps of the present invention, extremely low current densities are achieved at the points of application of said current and throughout the flow of current through the body, as have heretofore been unknown in the prior art. These extremely low current densities provide for a gentle push and pull on the ions of the tissue to which the current is applied, which does not overload the body's natural potential.

The method of the present invention also utilizes a long duty-cycle of between 0.00065 Hz and 0.00085 Hz. While alternating current is known in the prior art, no prior art teaches the utilization of such a long alternating current period. Experimentation by applicants has shown that a duty-cycle of 0.000732 Hz, or one cycle every 22.77 minutes, increases the body's ability to heal and regenerate tissue.

DETAILED DESCRIPTION OF PREFERRED EMBODIMENT OF INVENTION

The present invention provides for an apparatus consisting of various components. One component is an electrode wrap. Referring now to FIG. 1(a), an electrode wrap consists of a first and second layer wrap. The first and second layer wrap is applied to the selected portion of the body to which the current of the electrotherapy method of the present invention, or other electrotherapy method, is to be applied. The first and second layer wraps are applied in a manner such that a large surface area of the selected portion of the body is covered by said wrap. 101 The first layer wrap consists of a water-absorbent bandage. The bandage may be made of any material that easily absorbs and retains water, and may be of any length and width sufficient to completely wrap the portion of the body to which it is to be applied. 102 The second layer wrap consists of a moderately conductive, synthetic rubber impregnated cloth strap. The strap is of a length sufficient to wrap a large surface area of the selected portion of the body to which it will be applied. In a preferred embodiment, the second layer wrap is approximately two inches wide and twelve feet long, although other width and length wraps are contemplated by the present invention. In a preferred embodiment, the second layer wrap is composed of a cloth impregnated with silicon rubber acting as a flexible carrier for conductive carbon particles dispersed within the silicon rubber. The second layer wrap has a nominal resistance of 2 Kohms across the length of the wrap, as measured by any calibrated galvanic ohm meter.

Referring now to FIG. 1(b), when the 101 first and 102 second layer wrap are applied to the portion of the body to which the electrotherapy current will be introduced, they serve as a conductive surface around the selected portion of the body. Each electrode wrap is attached to either the positive or negative lead of the current output generator by 103 a means for conducting current, including, without limitation, copper wire, silver wire, iron wire, brass wire or aluminum wire. The electrode wraps are attached to the COG by alligator clips, button clips or other means in such a way that a complete circuit can be formed such that current will flow to one or more electrode wraps, then through the body, to the other one or more electrode wraps and then back to the COG. The current thus generated through the body creates a net force on the ions of the body in the path of the generated current through the body, thereby promoting healing and regeneration of the body's tissue. This current also has an effect in stimulating change to the body chemical structure by, among other things, reducing cortisol levels and increasing melatonin levels.

An apparatus is provided for by the present invention that supplies the current to be applied to the electrode wraps according to the method of the present invention. The preferred embodiment for this apparatus, the COG, is described below.

Figure 2:
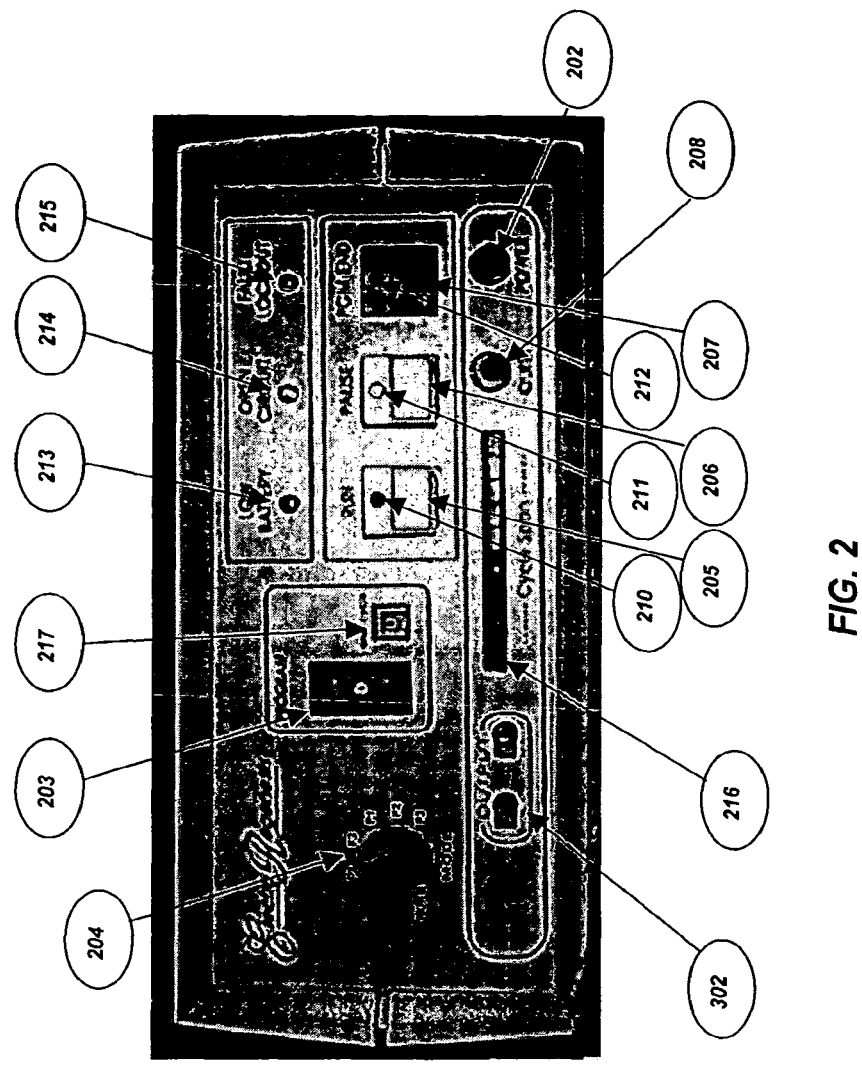
FIG. 2 is a picture of the user interface and display panel of the preferred current output generator of the present invention.
Figure 3:
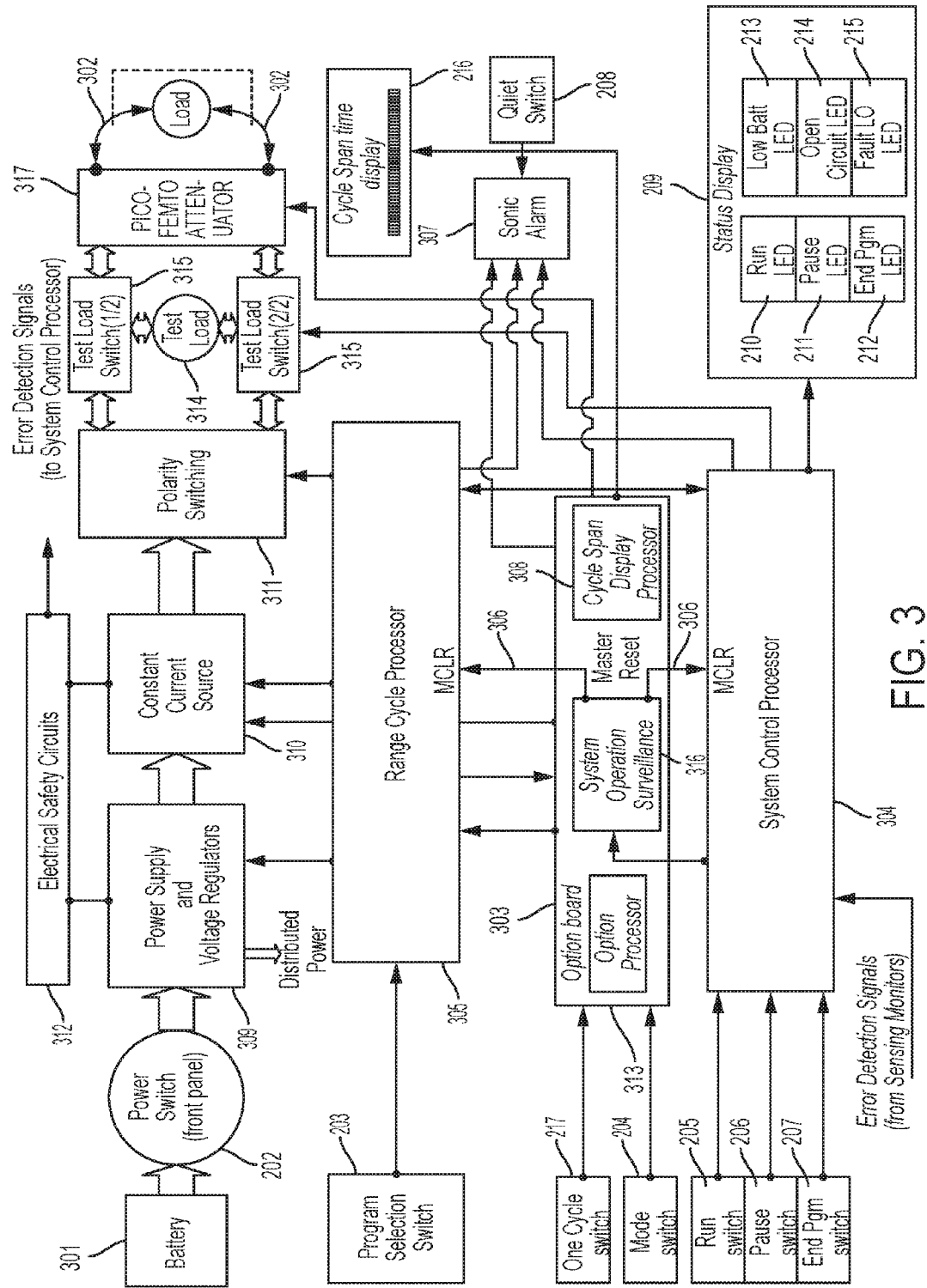
FIG. 3 is a diagram of components of the preferred current output generator of the present invention.

Referring now to FIG. 2 and FIG. 3, the COG has a preferred user interface. The user interface for the COG is contained on the 201 front of the COG casing. The user interface has a 202 power switch. The power switch can be of any of the various types of switching devices allowing for an on and off position. In a preferred embodiment, the power switch is a latching pushbutton switch. When the power switch is in the off position, no current is drawn from the batteries or other power supply for the COG. When the power switch is in the on position, the COG draws power from the 301 battery or other power supply and can generate a potential difference between the 302 positive and negative COG leads. When the power switch is turned to the on position the COG microprocessors receive power and begin a self-test sequence, as more fully described herein, to verify that the processors and safety monitors are functional. Until the self-test successfully executes, no treatment operation of the COG is possible.

The user interface also preferably contains a plurality of other switches. These switches can be any of the various types of switching devices that allow for two or more possible switching positions, for example, a latching or momentary push-button switch or multi-channel rotating switch. Further, the functionality of all switches may be incorporated into one multi-purpose switching device that can control all the functions of the plurality of independent switches.

A first switch is provided for in the present invention that is used to select the electrotherapy program to be applied as taught by the present invention. Preferably, the 203 program selection switch is a pushbutton thumbwheel switch. The program switch has sixteen different selection positions. Each position corresponds to a given level of current to be applied to the patient.

Another switch is provided for in the present invention that when utilized, in conjunction with the program selection switch, selects normal, Z mode, and three different femto modes of operation of the electrotherapy method of the present invention, allowing different ranges of current to be applied to the patient. Preferably, the 204 mode selection switch is a rotating thumbwheel switch. When utilized, the 204 mode selection switch sends a signal to the 313 option processor to change the operation of the COG to the selected mode. The 204 mode selection switch does not function to change modes of the COG when the COG is currently in a treatment cycle.

The sixteen positions of the 203 program selection switch, when in normal mode, selects one of thirteen possible current levels, comprising: 10 microamperes, 20 microamperes, 30 microamperes, 40 microamperes, 50 microamperes, 60 microamperes, 70 microamperes, 80 microamperes, 90 microamperes, 100 microamperes, 1 milliampere, 2 milliamperes and 3 milliamperes. When in normal mode, the last four positions of the 203 program selection switch all select the 3 milliampere current level. The sixteen positions of the 203 program selection switch, when in Z mode, selects one of ten possible current levels, comprising: 115 nanoamperes, 215 nanoamperes, 310 nanoamperes, 410 nanoamperes, 505 nanoamperes, 605 nanoamperes, 705 nanoamperes, 800 nanoamperes, 900 nanoamperes and 1000 nanoamperes. When in Z mode, the last six positions of the 203 program selection switch do not select any current level.

The 204 mode selection switch also has three possible pico modes. The three pico modes divide the current being supplied to the 302 COG output leads by activating the 317 femto-pico attenuator circuit. The 317 femto-pico attenuator circuit, when activated, divides the current of the Z mode operation by one thousand (pico1 mode), ten thousand (pico2 mode) and one hundred thousand (pico3 mode).

The sixteen positions of the 203 program selection switch, when in pico1 mode, selects one of ten possible current levels, comprising: 115 picoamperes, 215 picoamperes, 310 picoamperes, 410 picoamperes, 505 picoamperes, 605 picoamperes, 705 picoamperes, 800 picoamperes, 900 picoamperes and 1000 picoamperes. When in pico1 mode, the last six positions of the 203 program selection switch do not select any current level.

The sixteen positions of the 203 program selection switch, when in pico2 mode, selects one of ten possible current levels, comprising: 11.5 picoamperes, 21.5 picoamperes, 31 picoamperes, 41 picoamperes, 50.5 picoamperes, 60.5 picoamperes, 70.5 picoamperes, 80 picoamperes, 90 picoamperes and 100 picoamperes. When in pico2 mode, the last six positions of the 203 program selection switch do not select any current level.

The sixteen positions of the 203 program selection switch, when in pico3 mode, selects one of ten possible current levels, comprising: 1.15 picoamperes, 2.15 picoamperes, 3.1 picoamperes, 4.1 picoamperes, 5.05 picoamperes, 6.05 picoamperes, 7.05 picoamperes, 8 picoamperes, 9 picoamperes and 10 picoamperes. When in pico3 mode, the last six positions of the 203 program selection switch do not select any current level.

The 204 mode selection switch also has three possible femto modes. The three femto modes divide the current being supplied to the 302 COG output leads by activating the 317 femto-pico attenuator circuit. The 317 femto-pico attenuator circuit, when activated, divides the current of the Z mode operation by one million (femto1 mode), ten million (femto2 mode) and one hundred million (femto3 mode).

The sixteen positions of the 203 program selection switch, when in femto1 mode, selects one of ten possible current levels, comprising: 115 femtoamperes, 215 femtoamperes, 310 femtoamperes, 410 femtoamperes, 505 femtoamperes, 605 femtoamperes, 705 femtoamperes, 800 femtoamperes, 900 femtoamperes and 1000 femtoamperes. When in femto1 mode, the last six positions of the 203 program selection switch do not select any current level.

The sixteen positions of the 203 program selection switch, when in femto2 mode, selects one of ten possible current levels, comprising: 11.5 femtoamperes, 21.5 femtoamperes, 31 femtoamperes, 41 femtoamperes, 50.5 femtoamperes, 60.5 femtoamperes, 70.5 femtoamperes, 80 femtoamperes, 90 femtoamperes and 100 femtoamperes. When in femto2 mode, the last six positions of the 203 program selection switch do not select any current level.

The sixteen positions of the 203 program selection switch, when in femto3 mode, selects one of ten possible current levels, comprising: 1.15 femtoamperes, 2.15 femtoamperes, 3.1 femtoamperes, 4.1 femtoamperes, 5.05 femtoamperes, 6.05 femtoamperes, 7.05 femtoamperes, 8 femtoamperes, 9 femtoamperes and 10 femtoamperes. When in femto3 mode, the last six positions of the 203 program selection switch do not select any current level.

When in normal mode, the COG has a tolerance of plus or minus five percent for each current level selected. When in Z mode, pico mode or femto mode operation, the COG has a tolerance level of plus or minus fifteen percent. For the first ten positions of the program selection switch indicated above, whether in Z mode, normal mode or any pico or femto mode, the patient or other operator of the COG can select single cycle or repeating cycle modes. For these positions, the present invention provides for a 217 one cycle switch that selects either one cycle or repeating mode. The 217 one cycle switch is preferably a latching pushbutton switch. The operation of the COG is limited to only one cycle mode for the last six positions of the program selection switch. When utilized, the 217 one cycle switch sends a signal to the 303 option processor indicating that no further treatment cycles should be started after conclusion of the present treatment cycle.

Another switch is provided for in the present invention that begins the treatment cycle of the electrotherapy method of the present invention. Preferably, this 205 switch is a momentary pushbutton switch. When utilized, the 205 run program switch sends a signal to the 304 system control processor indicating that the treatment cycle should begin. If certain safety conditions described more fully herein are met, the COG will deliver current to the 302 COG output leads according to the mode that has been selected with the other switches.

Another switch is provided for in the present invention that when utilized will pause the electrotherapy treatment cycle. When the 206 pause switch is utilized, a signal is sent to the 304 system control processor to halt output of current to the COG leads. The time remaining in the treatment cycle is stored by 305 the range cycle processor. When the patient or other operator of the COG wishes to resume the paused treatment, the 206 pause switch is again selected to unpause the treatment cycle. A signal is then sent to the 304 system control processor. If certain safety conditions described more fully herein are met, the output of current to the 302 COG leads is resumed and the treatment cycle continues.

Another switch is provided for in the present invention that when utilized will end the electrotherapy treatment cycle. Preferably, the 207 program end switch is a momentary pushbutton switch. When the 207 program end switch is utilized, a signal is sent to the 304 system control processor to reset the COG. The 304 system control processor activates the 306 master reset line. The 306 master reset line is attached to the manual reset pin of each microprocessor of the COG. Activation of the program end switch causes all the COG microprocessors to reset and all current output to cease.

Another switch is provided for in the present invention that when utilized lowers the sound level of the 307 sonic alarm of the COG. Preferably, the 208 quiet switch is a latching pushbutton switch. If the 307 sonic alarm is presently unquieted, when the 208 quiet switch is utilized a signal is sent to the 307 sonic alarm to reduce the voltage provided to the speaker. If the 307 sonic alarm is presently quieted, when the 208 quiet switch is utilized a signal is sent to the 307 sonic alarm to increase the voltage provided to the speaker.

The 201 user interface for the COG also preferably has a status display. 209 A status display aids the patient or other operator in the utilization of the COG and microcurrent electrotherapy method of the present invention. The status display preferably has six status indicators. The status indicators are preferably LED devices, such as a Kingbright® L-1154 round LED lamp, that light in certain situations. The 209 status display communicates with and receives commands from the 304 system control processor. In order to conserve battery power, the LED status indicators are not continually lit, but flash for a very short duration, typically 1/100th of a second, every five seconds.

One status indicator 210 is used to indicate when the COG is supplying current to the 302 COG output leads, and the electrotherapy method is in progress. Another status indicator 211 is used to indicate a pause in the electrotherapy method by either the patient or other operator of the COG. Another status indicator 212 is used to indicate when the electrotherapy treatment has been completed and the COG is no longer supplying current to the 302 COG output leads. Another status indicator 213 is used to indicate that the battery supplying the power to the COG is running low and should be replaced or recharged. Another status indicator 214 is used to indicate when the circuit formed by attaching the electrode wraps to the 302 COG leads by means for conducting electrical current is open, and hence the COG cannot supply current to the electrode wraps. Another status indicator 215 is used to indicate that a fault lockout has occurred.

The COG also preferably has a 216 cycle span time display. The cycle span time display indicates to the patient or other operator of the COG the duration and time remaining in the treatment cycle. The 216 cycle span time display is preferably a bar graph segmented LED display, such as a Kingbright® DC-10 bar graph array. The 216 cycle span time display communicates with and receives instructions from the 308 cycle span display processor. For a ten segment LED display, each segment represents a period of approximately ten percent of the cycle time. Each segment is lit when the time period that the segment represents is entered. Once an LED segment is lit, it remains lit until the entire cycle span time display is reset. For example, at the beginning of the treatment cycle the first LED segment is lit. The second LED segment is lit after ten percent of the cycle time has elapsed, so that the first and second LED segments are now lit. The third LED segment is lit after twenty percent of the cycle time has elapsed, so that the first, second and third LED segments are now lit. This continues until the last LED segment is lit when ninety percent of the cycle time has elapsed, so that all the LED segments are lit. When every LED segment is lit, the patient is thereby informed that the current treatment cycle is nearing completion. If the patient or other operator has selected repeating cycle mode, the 313 option processor will send a command to the 308 cycle span display processor to reset the 216 cycle span time display and begin incrementing again. In order to conserve battery power, the 216 cycle span time display is not continually lit, but flashes approximately every 20 seconds for a duration of 1 second.

The COG preferably has a 307 sonic alarm. The 307 sonic alarm may consist of a speaker attached electrically to a wave generator. Preferably, the 307 sonic alarm is a piezo-buzzer, that emits a short beep. However, other devices for making sounds are contemplated by the present invention. The 307 sonic alarm communicates with and receives instructions from the certain processors of the COG. Preferably, the processors that communicate with the 307 sonic alarm are the 304 systems control processor, the 313 option processor and the 305 range cycle processor. On the occurrence of certain events, the appropriate systems processor sends an instruction to the 307 sonic alarm indicating that said event has occurred. The 307 sonic alarm processes the incoming signal, and outputs an appropriate signal to the speaker. The speaker then outputs an appropriate aural indicator.

As an example, consider the case where a patient starts an electrotherapy treatment cycle and then falls asleep. If the patient has set the COG to one cycle mode, the COG will automatically terminate after one treatment cycle. When the COG completes the one cycle, a signal is sent from the 305 range cycle processor to the 307 sonic alarm, instructing it to send a signal that one cycle is completed. The 307 sonic alarm then generates a wave signal that is sent to the speaker. The speaker then makes that signal aural, informing the sleeping patient that a cycle has been completed. In this way, a patient that is sleeping, or otherwise unable to see the progress of the treatment cycle on the 216 cycle span time display, can be informed of the end of a treatment cycle.

Other aural indicator functions for the sonic alarm are contemplated by the present invention. These functions include, but are not limited to, low battery power, open circuit, current out of tolerance level, fault lockout and end of program. On the occurrence of any of these events, the appropriate system processor sends a command to the wave generator. The 307 sonic alarm processes the incoming signal, and outputs an appropriate signal to the speaker. The speaker then outputs an appropriate aural indicator.

The COG is preferably supplied power by 301 battery. The 301 battery is preferably a six volt rechargeable battery. The COG does not draw current from the battery until the 202 power switch of the 201 user interface is set in the on position. Once the power switch is in the on position, current flows to the 309 power supply and voltage regulator. The 309 power supply and voltage regulators distributes power and maintains adequate voltage throughout the circuitry of the COG. The 309 power supply and voltage regulator communicate with and receive instructions from the 305 range cycle processor. The COG operates for approximately 50 hours on one charge of the 301 preferred battery.

The present invention also provides for a 310 constant current source. The 310 constant current source provides a constant current to the 311 polarity switching device. This constant current provided by the 310 constant current source is preferably within the tolerances of the selected program from the 203 program selection switch. The 310 constant current source communicates with and receives instructions from the 305 range cycle processor.

The 310 constant current source preferably consists of a voltage reference, a current sensing device, an amplifier, control element and output current source. The current sensing device signals are sent to the amplifier and then are compared to the reference voltage. A control signal is derived from the comparison and sent to the control element to adjust to the correct voltage value for the selected current range. In the case where the current measured by the current sensing device is outside the tolerance range of the selected program, the amplifier sends a signal to the control element to either increase or decrease the voltage being created between the 302 COG leads, thereby bringing the current being supplied to the 302 COG leads within the tolerance set by the selected program. In this way the constant current source is able to continually adjust to any change in the load present on the 302 COG output leads, thereby maintaining an acceptable current output.

The present invention also provides for 312 a plurality of electrical safety circuits. These circuits are continuously active and constantly measures various performance levels of the COG. In a preferred embodiment the COG internal operating voltage is monitored for a minimum acceptable voltage. If the internal operating voltage falls below this level, the 312 electrical safety circuit sends a signal to the 304 system control processor indicating that low system voltage has been detected. The power source voltage being supplied to the 310 constant current source is also monitored by the 312 electrical safety circuits for an acceptable maximum voltage. If the voltage is above this level, the 312 electrical safety circuit sends a signal to the 304 system control processor indicating that over voltage has been detected. The current being supplied to the 302 COG output leads is also monitored by the 312 electrical safety circuits for maximum safe current levels. In a preferred embodiment the maximum safe current level varies with the selected treatment current level, i.e. approximately 20% above the current level of the selected treatment program. If the current being supplied to the 302 COG output leads is measured to be above this maximum safe current level, a signal is sent to the 304 system control processor indicating that the current is being supplied to the 302 COG output leads is above the safe current level range.

The present invention provides for a 305 range cycle processor. The 305 range cycle processor is a microprocessor, such as a CMOS microprocessor, programmed to operate according to the method and requirements of the present invention. The 305 range cycle processor receives data from the 203 program selection switch indicating which program should be run. The 305 range cycle processor passes the selected program current level information to the 310 constant current source and to the 304 system control processor. The 305 range cycle processor also controls the cycle time of the COG. Specifically, the 305 range cycle processor sets the cycle time to 0.000732 Hz. The 305 range cycle processor controls the 311 polarity switching circuit, causing the current flow to be reversed every half-cycle. When the 305 range cycle processor receives a pause signal from the 206 pause switch, the 305 range cycle processor halts the cycle time. When the 305 range cycle processor receives an unpause signal from the 206 pause switch, the 305 range cycle processor continues the cycle time.

The present invention provides for a 303 option board. The 303 option board is comprised of an 313 option processor and a 308 cycle span display processor attached to a circuit board. The 313 option processor is a microprocessor, such as a CMOS microprocessor, programmed to operate according to the method of the present invention. In a preferred embodiment, the 313 option processor receives signals from the 217 one cycle switch and 204 mode switch. When a signal is received from the 204 mode switch, the 313 option processor changes the mode of operation of the COG. When the 313 option processor receives a signal from the 217 one cycle switch, provided certain safety condition as more fully described herein are met, the 313 option processor changes the COG operation from one cycle mode to repeating cycle mode or from repeating cycle mode to one cycle mode as appropriate.

The 308 cycle span display processor is a microprocessor, such as a CMOS microprocessor, programmed to operate according to the method of the present invention. The 308 cycle span display processor monitors the elapsed time in each treatment cycle. The 308 cycle span display processor sends instructions to the 216 cycle span time display to light the next LED segment after an appropriate time has elapsed, e.g. at the beginning of each 1/10th of the cycle time for a 10 segment LED display. The 308 cycle span display processor also resets the 216 cycle span time display after the termination of each treatment cycle.

Alternatively, the 303 option board may also include a 316 systems operation surveillance circuit. The 316 systems operation surveillance circuit is an inter-microprocessor analog circuit. The 316 systems operation surveillance circuit acts as a surveillance timer for the COG. In a preferred embodiment the 316 systems operation surveillance circuit receives periodic signals from the 304 system control processor, i.e. one signal every 30 seconds. If the 316 systems operation surveillance circuit fails to receive a periodic signal from the 304 system control processor, the 316 systems operation surveillance circuit times out. This time out indicates that the performance of the 304 system control processor cannot be validated. When the 316 systems operation surveillance circuit times out, a manual reset signal is sent to each of the COG processors via the 306 manual reset line to terminate all operations and reset. The COG must then successfully run a self-test in order to restart operations.

The present invention provides for a 304 system control processor. The 304 system control processor is a microprocessor, such as a CMOS microprocessor, programmed to operate according to the method and requirements of the present invention. The 304 system control processor receives from the 312 electrical safety circuits a signal indicating the voltage across the terminals of the 301 COG battery. If the received signal indicates a significant voltage drop across the battery terminals, i.e. voltage lower than 5.8 volts DC for a six volt battery, the 304 system control processor sends a signal to the 307 sonic alarm to aurally indicate that the 301 battery should be recharged and sends a signal to the 213 low battery LED of the 209 status display to light and visually indicate that the 301 battery should be recharged. If the received signal indicates a substantial voltage drop across the battery terminals, i.e. voltage lower than 4.6 volts DC, the 304 system control processor sends a signal, via the 306 master reset line, to reset all COG microprocessors and halt further operation of the COG. The COG will be inoperable until the 301 battery has been replaced or recharged to an acceptable voltage level, i.e. approximately 5.8 volts DC.

The 304 system control processor also operates as an error sensor for the COG. The 304 system control processor receives other signals from the 312 electrical safety circuits. If an error signal, as discussed above, is received by the 304 system control processor, the 304 system control processor halts system operation. The 304 system control processor then isolates the output to the 302 COG leads from the rest of the COG circuitry so no potential difference exists between said leads. The 304 system control processor then sends a signal to the to the 307 sonic alarm to aurally indicate that a COG fault lockout has occurred and sends a signal to the 215 fault lockout LED of the 209 status display to light and visually indicate that a COG fault lockout has occurred. If a COG fault lockout occurs, the COG remains inoperable until the indicated errors are corrected.

Particularly, a fault lockout will occur if the internal system operating voltage is measured below a minimum acceptable level, i.e. below 5.0 volts DC. A fault lockout will also occur when the current level as measured between the 302 COG leads is above a maximum acceptable level, i.e. 20% above the current level of the selected treatment program current level.

In a preferred embodiment the COG is monitored for an open circuit between the 302 COG output leads. If an open circuit is detected between the 302 COG output leads by the 312 electrical safety circuits, a signal is sent to the 304 system control processor indicating that there is an open circuit between the 302 COG output leads. If the 304 system control processor receives an open circuit signal, the 304 system control processor sends a signal to the 307 sonic alarm to aurally indicate that a complete circuit is not being made between the leads and sends a signal to the 214 open lead LED of the 209 status display to light and visually indicate that a complete circuit is not being made between the leads.

The 304 system control processor also monitors the 205 run, 206 pause and 207 program end switches, and controls the COG operation accordingly. When the 205 run switch is utilized, a signal is sent to the 304 system control processor to begin the selected program treatment. Provided certain safety condition are met, as are herein more fully described, the 304 system control processor begins the selected treatment cycle and sends appropriate signals to the rest of the COG circuitry. The 304 system control processor then sends a signal to the 210 run LED of the 209 status display to light and visually indicate that the COG is providing current to the 302 COG leads. When the 206 pause switch is first utilized, a signal is sent to the 304 system control processor to pause the current treatment cycle. The 304 system control processor then halts the current treatment cycle and sends appropriate signals to the rest of the COG circuitry. The 304 system control processor then sends a signal to the 211 pause LED of the 209 status display to light and visually indicate that the selected treatment cycle is paused. When the 206 pause switch is utilized again, a signal is sent to the 304 system control processor to unpause the current treatment cycle. The 304 system control processor then resumes the current treatment cycle and sends appropriate signals to the rest of the COG circuitry. The 304 system control processor then sends a signal to the 211 pause LED of the 209 status display to unlight. When the 207 program end switch is utilized, a signal is sent to the 304 system control processor to terminate the current treatment cycle. The 304 system control processor then terminates the current treatment cycle and sends appropriate signals to the rest of the COG circuitry. The 304 system control processor then sends a signal to the 212 program end LED of the 209 status display to light and visually indicate that the current treatment cycle has terminated. The 304 system control processor then begins the system self test and prepares for a new cycle of operation.

In order to receive full efficacy of the present electrotherapy method and apparatus, it is important for the treatment current levels to be within the tolerances of the present invention. If the circuitry of the COG is not operating properly, it is possible that the electric current being provided to the body can be outside the specified ranges. Accordingly, the present invention provides for 312 electrical safety circuits, as detailed above, to monitor and ensure safe system performance. In a preferred embodiment, the COG also provides for a self-test of the 312 electrical safety circuits. The 304 system control processor performs a self-test of the 312 electrical safety circuits monitoring during start-up of the COG and following a manual reset of the COG.

In conducting the self-test, the 304 system control processor instructs the 302 output leads of the COG to be removed from the 310 current source and 311 polarity switching device by activating the 315 test load switches. 314 Test loads are then connected to the 310 current source and 311 polarity switching device. These 314 test loads are designed to cause the current through the test loads to exceed the maximum safety limits of the COG. If the self-test fails, i.e. the 312 electrical safety circuits fail to return an error, the 304 system control processor causes a fault lockout to occur. The 304 system control processor then isolates the 302 output to the COG leads from the rest of the COG circuitry so no potential difference exists between said leads. The system control processor then sends a signal to the 307 sonic alarm to aurally indicate that a COG fault lockout has occurred and sends a signal to the 215 fault lockout LED of the 209 status display to light and visually indicate that a COG fault lockout has occurred. If a COG fault lockout occurs, the user may not utilize the COG until the error is corrected and the self-test is properly performed.

If the self-test properly executes, i.e. an error signal is generated by the 312 electrical safety circuits and received by the 304 system control processor, the 304 system control processor deactivates the 315 test load switches, reconnecting the output of the 310 constant current source and 311 polarity switching device to the 302 COG output leads. After a successful self-test, the COG is ready for use.

Referring again to FIG. 1(*a*), the method of the present provides for the application of a large surface-area electrode wrap. Preferably, said electrode wrap comprises a 101 first and 102 second layer wrap. Preferably, the patient soaks the 101 first layer wrap with tap water prior to application. After saturating the 101 first layer wrap with tap water, the patient wraps the 101 first layer wrap around the portion of the body to which the current will be applied. This can be any part of the body, including, without limitation, the head, arm, leg, feet, hand and torso. The application of tap water to the 101 first layer wrap provides good conductivity to the layer being placed closest to the skin. Tap water is a moderately good conductor of electricity on account of the metal ions contained in the tap water.

Figure 1:
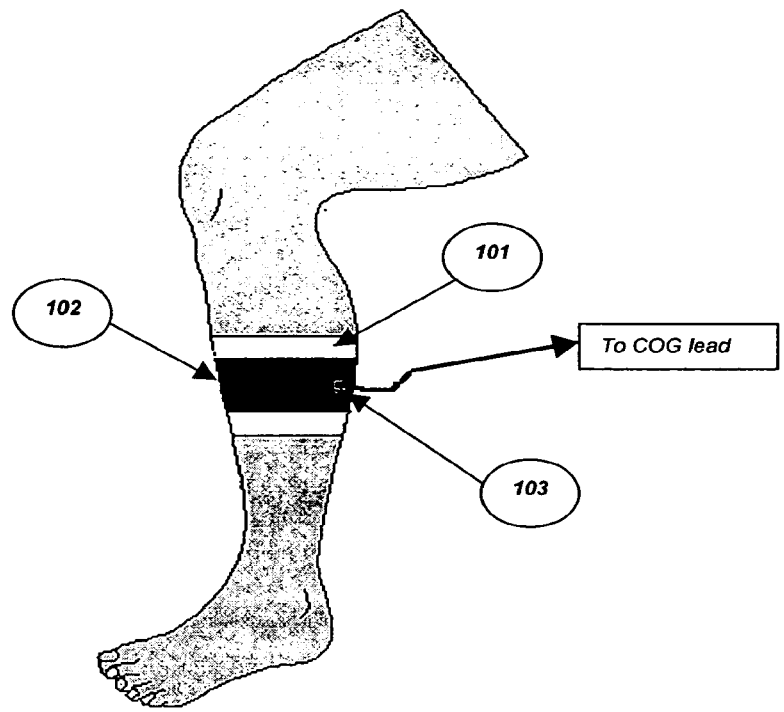
FIG. 1(a) is a depiction of the preferred electrode wrap as taught by the present invention.
FIG. 1(b) is a drawing of the preferred method of application of the electrode wrap.
Figure 1:
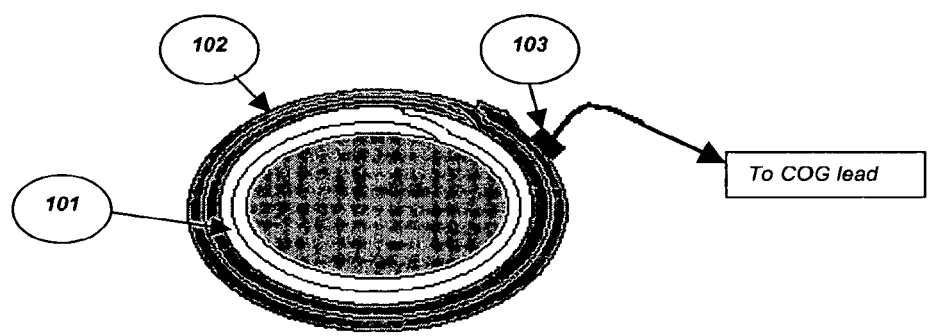

Once the 101 first layer wrap is applied to the selected portion of the body, the 102 second layer wrap is applied over the 101 first layer wrap. This 102 second layer wrap is a moderately conductive synthetic rubber impregnated cloth strap. In a preferred embodiment, the 102 second layer wrap is composed of a cloth impregnated with silicon rubber acting as a flexible carrier for conductive carbon particles dispersed within the silicon rubber. The 102 second layer wrap has 103 one or more electrodes on its distal ends to which it can be electrically connected with the COG by means for conducting electricity. Referring now to FIG. 1(*b*), when properly applied, the 101 first and 102 second layer wrap form an cylindrical surface around the selected portion of the body.

Because the first and second layer wraps, as taught by the present invention, are only moderately good conductors, the current is spread out over a large surface-area. Due to this large surface-area and moderate conductivity of the first and second layer wraps, the point of entry and exit of the current is spread across a broad surface area of the selected portions of the body. Thus, a very low current density around the selected portions of the body is thereby achieved through the present invention. As one example, 500 square inches of body surface is covered by one of the electrode wraps and a current of 500 nanoamperes is applied through the body via the first and second layer wraps, resulting in a current density of 1 nanoampere per square inch at each selected portion of the body. These low current densities are translated into substantially lower current densities through the body as the current travels from the electrode wrap(s) attached to the positive COG lead to the electrode wrap(s) attached to negative COG lead than has been previously achieved by known electrotherapy techniques. These low current densities do not overload the body's natural electropotential, but instead provide a slight push and pull on the body's natural current, thereby aiding the body's natural healing process.

The electrotherapy method of the present invention utilizes a microcurrent to effectuate the healing of the tissue. The microcurrent that is applied to the body is in the range of 3 milliamperes to 1 femtoampere. The use of current lower than 20 microamperes is unknown to the prior art. Specifically, the inventors have discovered that use of current in the range of 100 to 500 nanoamperes results in improved healing of the body tissue in comparison to prior art electrotherapy techniques.

The electrotherapy method of the present invention utilizes a duty cycle in the range of 0.00065 to 0.00085 Hz. Preferably, a duty cycle of 0.000732 Hz is utilized. This translates to a cycle time of 22.77 minutes. Experimentation has shown that a duty cycle of 0.000732 Hz, plus or minus ten percent, has an improved healing effect on the body tissue over the application of the same current at a different duty cycle, with markedly increased healing being achieved by a duty cycle of 0.007732 Hz, plus or minus two percent. Experimentation has shown that the efficacy distribution of the method of the present invention is Gaussian in the range of plus and minus ten percent of 0.000732 Hz.

EXPERIMENTAL

Applicants have performed the following experiments using the electrotherapy apparatus and method of the present invention. Results from these experiments, which are typical of the beneficial results of the present invention, are detailed below in Table 1.

TABLE 1

| Patient | Disease | Stage | Number Months Present | Time to Heal |
|---|---|---|---|---|
| 1 | DM | 3 | 6 | 70% in 48 hours |
| 2 | DM | 4 | 60 | 50% in 2 weeks |
| 3 | DM | 4 | 36 | 60% in 1 week |
| 4 | SCI | 3 | 9 | 100% in 48 hours |
| 5 | SCI | 4 | 3 | 40% in 12 days |
| 6 | PVD | 4 | 9 | 90% in 72 hours |
| 7 | PVD | 4 | 12 | 100% in 5 days |
| 8 | SCI | 4 | 18 | 75% in 7 days |
| 9 | DM | 3 | 8 | 100% in 72 hours |

All patients included in Table 1 have decubitus ulcers. The primary disease leading to the ulcers is indicated in the second column, as follows: DM indicates diabetes mellitus, SCI indicates spinal cord injury and PVD indicates peripheral vascular disease. The size of the ulcers is indicated by the stage listed in the third column. The indicated stages are based on the scale developed in 1989 by the National Pressure Ulcer Advisory Panel Consensus. A stage 3 ulcer consists of full thickness skin loss involving damage to or necrosis of subcutaneous tissue that may extend down to, but not through, underlying fascia. A stage 3 ulcer present clinically as a deep crater with or without undermining adjacent tissue. A stage 4 ulcer consists of full thickness skin loss with extensive destruction, tissue necrosis, or damage to muscle, bone or supporting structures. Stage 4 ulcers may be associated with undermining of adjacent tissue and sinus tracts. The length of time the ulcers have been present in the listed stage is indicated in the fourth column.

Each patient underwent a treatment program utilizing the electrotherapy apparatus and method of the present invention. The typical treatment program consisted of three and one-half hours of treatment per day, five days per week. The results of the treatment program are given in the fifth column of Table 1. The percentage indicated in the fifth column is the approximate percentage of ulcer closure in terms of depth and diameter. As can be seen from Table 1, the use of the electrotherapy apparatus and method of the present invention gives beneficial results in the healing of persistent ulcers of various pathologies.

Although the foregoing invention has been described in some detail by way of illustration and example for purposes of clarity of understanding, it will be obvious that certain changes and modifications may be practiced within the scope of the appended claims.

All publications, patents, and patent applications are herein incorporated by reference in their entirety to the same extent as if individual publication, patent, or patent application was specifically and individually indicated to be incorporated by reference in its entirety.

We claim:

1. In an electrotherapy method wherein an electrode is placed proximate to a damaged tissue mass, or on the surface of the skin, that is contiguous with said damaged tissue mass, a microcurrent applied through said electrode to said damaged tissue mass, in accordance with a defined treatment regime, and the method repeated, as needed, to promote healing of said damaged tissue mass, wherein the improvement comprises:

A. Providing
  (i) a body conformable, electrode wrap of composite construction consisting essentially of a first layer including a moisture absorbent material for placement proximate to a damaged tissue mass, a second layer of elastomeric material, in electrical contact with said first layer and a source of direct electrical current, said second layer including a dispersion of conductive particles within said elastomeric material, and means, associated with said second layer, for connecting said electrode to said source of direct electric current;
  (ii) means for connecting said source of direct electric current connected to said electrode wrap;
  (iii) means for activating said electrode wrap with electrical energy from said source of direct electric current;
  (iv) means for periodically reversing polarity of said direct electric current so as to produce an alternating current; and
  (v) means for inactivating said electrode wrap, thereby terminating flow of the direct electric current to said electrode wrap, from said source of direct electric current;

B. Saturating said first layer of said electrode wrap with water;

C. Placing said electrode wrap upon an individual for treatment of a damaged tissue mass so as to essentially completely encircle said damaged tissue mass with said electrode wrap; and D. Applying the alternating current with a duty cycle of 0.00065 Hz to 0.00085 Hz, to said electrode wrap, in accordance with a therapeutic protocol, so as to effect essentially uniform dispersal of electrical energy within said second layer of said electrode wrap, and, thereby, over said first layer of said electrode wrap proximate to said damaged tissue mass, with the proviso that each of said first and each of said second layer of said wrap are essentially coextensive with one another, and otherwise conform to a portion of an individual's body so as to provide an essentially uniform pattern of therapeutic energy distribution; and E. Repeating Step (D) at least one additional time.

2. The method of claim 1, wherein Step (D) comprises applying the alternating current with a current density of less than 5 microamperes per square inch of said electrode wrap, to the individual in need thereof.

3. The method of claim 1, wherein Step (D) comprises applying the alternating current of 1 femtoampere to 20 microamperes, with a duty cycle of 0.00065 Hz to 0.00085 Hz and at a current density of less than 5 microamperes per square inch of said electrode wrap.

4. In a system for providing therapeutic effective amounts of electrical energy to a damaged tissue mass to promote regeneration and healing of said damaged tissue mass, wherein the improvement comprises:
 A. A body conformable, electrode wrap of composite construction consisting essentially of a first layer including a moisture absorbent material for placement proximate to a said damaged tissue mass, a second layer of elastomeric material, in electrical contact with said first layer and a source of direct electrical current, said second layer including a dispersion of conductive particles within said elastomeric material and means, associated with said second layer for connecting said electrode wrap to said source of direct electric current;
 B. Means for activating said electrode wrap with electrical energy from said source of direct electric current;
 C. Means for periodically reversing polarity of said direct electric current so as to produce an alternating current;
 D. Means for inactivating said electrode wrap, thereby terminating flow of said direct electric current to said electrode wrap, from said source of direct electric current; and
 E. Means for execution of an electrotherapy protocol for modulation of delivery of the alternating current with a duty cycle of 0.00065 Hz to 0.00085 Hz, from a source thereof, to said electrode wrap and from said electrode wrap to said damaged tissue mass;
and
 F. Means for monitoring of delivery of therapeutic effective amounts of said alternating current through said electrode wrap to said damaged tissue mass, with the proviso that each of said first and each of said second layer of said electrode wrap are essentially coextensive with one another, and otherwise conform to a portion of an individual's body so as to provide an essentially uniform pattern of therapeutic energy distribution.

* * * * *